United States Patent [19]

Daugan et al.

[11] Patent Number: 5,435,806

[45] Date of Patent: * Jul. 25, 1995

[54] DIAPER PROVIDED WITH AN IMPROVED ELASTIC FITTING

[75] Inventors: Jean P. Daugan, Bougival; Leroy Francis, Cergy, both of France

[73] Assignee: Colgate-Palmolive Company, New York, N.Y.

[ * ] Notice: The portion of the term of this patent subsequent to Oct. 28, 2011 has been disclaimed.

[21] Appl. No.: 264,004

[22] Filed: Jun. 22, 1994

Related U.S. Application Data

[63] Continuation of Ser. No. 33,961, Mar. 19, 1993, Pat. No. 5,324,277, which is a continuation of Ser. No. 576,175, Aug. 30, 1990, abandoned, which is a continuation of Ser. No. 309,939, Feb. 10, 1989, abandoned, which is a continuation of Ser. No. 912,881, Sep. 26, 1986, abandoned.

[51] Int. Cl.⁶ .................... A61F 13/15; A61F 13/20
[52] U.S. Cl. .................... 604/385.2; 604/358; 604/367; 604/369; 604/373; 604/385.1
[58] Field of Search .................... 604/358, 367–369, 604/378, 385.1, 385.2, 373

[56] References Cited

U.S. PATENT DOCUMENTS

| | | |
|---|---|---|
| Re. 31,922 | 6/1985 | Mesek et al. . |
| 2,581,904 | 1/1952 | Burns . |
| 3,400,718 | 9/1968 | Seijo . |
| 3,688,767 | 9/1972 | Goldstein . |
| 3,860,003 | 1/1975 | Buell . |
| 3,995,638 | 12/1976 | Schaar . |
| 4,014,338 | 3/1977 | Schaar . |
| 4,050,462 | 9/1977 | Woon . |
| 4,205,679 | 6/1980 | Repke et al. . |
| 4,246,900 | 1/1981 | Schroder . |
| 4,285,342 | 8/1981 | Mesek . |
| 4,300,562 | 11/1981 | Pheniak . |
| 4,323,070 | 4/1982 | Ternstrom et al. . |
| 4,324,245 | 4/1982 | Mesek et al. . |
| 4,325,372 | 4/1982 | Teed . |
| 4,333,782 | 6/1982 | Pieniak . |
| 4,337,771 | 7/1982 | Pieniak et al. . |
| 4,338,938 | 7/1982 | Seavitt . |
| 4,352,355 | 10/1982 | Mesek et al. . |
| 4,388,075 | 6/1983 | Mesek et al. . |
| 4,405,397 | 9/1983 | Teed . |
| 4,407,284 | 10/1983 | Pieniak . |
| 4,413,623 | 11/1983 | Pieniak . |
| 4,425,127 | 1/1984 | Suzuki et al. . |
| 4,430,086 | 2/1984 | Repke . |
| 4,500,316 | 2/1985 | Damico . |
| 4,515,595 | 5/1985 | Kievit et al. . |
| 4,582,550 | 4/1986 | Sigi . |
| 4,585,447 | 4/1986 | Karami . |
| 4,585,448 | 4/1986 | Enloe . |

(List continued on next page.)

FOREIGN PATENT DOCUMENTS

| | | |
|---|---|---|
| 2289131 | 10/1975 | France . |
| 2388515 | 4/1978 | France . |
| 2421571 | 3/1979 | France . |
| 2085281 | 10/1980 | United Kingdom . |
| 2130888 | 11/1982 | United Kingdom . |

Primary Examiner—Randall L. Green
Assistant Examiner—P. Zuttarelli
Attorney, Agent, or Firm—Connolly & Hutz

[57] ABSTRACT

This diaper comprises at the level of each of its transverse edges, a strip of open cell foam material extending transversely with respect to the diaper and fixed between the support and upper sheets of the latter. These elastic strips are designed to come into elastic contact with the body of a user at the level of the latter's waist. The longitudinal inner and outer edges of each strip communicate respectively with the inner space of the napkin and with the outside of the latter to permit this inner space to communicate thus with the outer space through the thickness of the strips so as to permit the internal ventilation of the napkin.

5 Claims, 2 Drawing Sheets

U.S. PATENT DOCUMENTS

| | | |
|---|---|---|
| 4,606,964 | 8/1986 | Wideman . |
| 4,610,745 | 9/1986 | Sallee et al. . |
| 4,639,949 | 2/1987 | Ales et al. . |
| 4,652,487 | 3/1987 | Morman . |
| 4,681,580 | 7/1987 | Reising et al. . |
| 4,685,916 | 8/1987 | Enloe . |
| 4,710,189 | 12/1987 | Lash . |
| 4,726,807 | 2/1988 | Young et al. . |
| 4,753,646 | 6/1988 | Enloe . |
| 4,762,521 | 8/1988 | Roessler et al. . |
| 4,808,252 | 2/1989 | Lash . |
| 4,846,827 | 7/1989 | Sallee et al. . |
| 4,909,804 | 3/1990 | Douglas, Sr . |
| 4,917,682 | 4/1990 | Lancaster et al. . |
| 4,938,754 | 7/1990 | Mesek . |
| 5,188,626 | 2/1993 | Toyoda et al. .................. 604/358 |
| 5,246,432 | 9/1993 | Suzuki et al. . |
| 5,324,277 | 6/1994 | Daugan et al. .................. 604/385.1 |

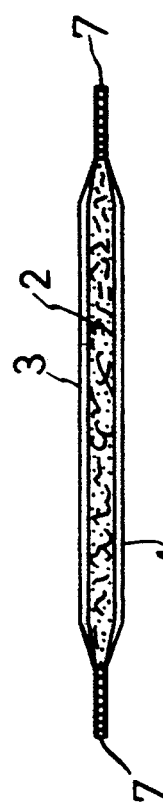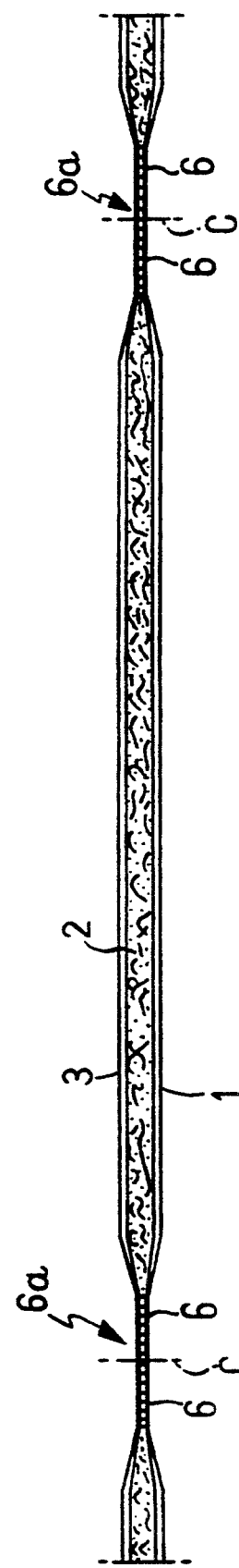

DIAPER PROVIDED WITH AN IMPROVED ELASTIC FITTING

CROSS-REFERENCE TO RELATED APPLICATIONS

This application is a continuation of application Ser. No. 08/033,961 filed Mar. 19, 1993, now U.S. Pat. No. 5,324,277; which in turn is a continuation of Ser. No. 07/576,175 filed Aug. 30, 1990, now abandoned; which in turn is a continuation of Ser. No. 07/309,939 filed Feb. 10, 1989, now abandoned; which in turn is a continuation of Ser. No. 06/912,881 filed Sep. 26, 1986, now abandoned.

BACKGROUND OF THE INVENTION

1. Field of the Invention

The present invention relates to diapers (or napkins), particularly discardable diapers, comprising a flexible and impermeable support sheet, a flexible and permeable upper sheet joined to the support sheet over at least a portion of the periphery of the diaper. A pad of absorbent material is placed between the upper sheet and the support sheet and elastic means positioned over at least a portion of the periphery of the diaper designed to be applied elastically onto the body of a user of this diaper.

2. Description of the Prior Art

Numerous diapers are now found provided with elastic members at the level of the crotch designed to form a barrier around the thighs of the user of the diaper. Such diapers have different shapes; thus, they may be rectangular with longitudinal edges, as the case may require, folded back to reduce the width at the crotch or have a cut-out at the level of this crotch in order to reduce the width of the diaper and thus to constitute a so-called anatomical shape.

These diapers provided with elastic elements at the crotch are generally well adapted to the body of the user and do not show leakages around the thighs at least when they are not saturated with liquid or poorly positioned.

However, leakages frequently occur around the waists of babies according to the position of the latter. Such leakages are associated with the morphology of the baby, who does not have a muscular abdominal belt. In spite of all the precautions which can be taken on the placing in position of the napkin, the latter, which is capable of being distorted at the level of the waist, begins, after a certain number of changes in position of the baby, to gape at the level of the waist of the latter which thus results in risk of leakages in the following cases:

Direct leakages especially in reclining position. The flow rate of the urination, generally being very much greater at the level at which the urine flows through the permeable upper sheet, the urinary liquid escapes at the spot where the complete change is not tight. This type of leakage can also occur on occasional pressure exerted on the absorbent material of the pad when the alter is close to saturation;

Direct leakages by directional orientation of the urination stream towards the place at the waist of the in fact where the diaper has a tendency to gape, which is the case with boys;

Leakage by capillary pumping when an undergarment of hydrophilic material slips between the skin and the diaper which gapes at the level of the waist.

To avoid such leakages and to apply the corresponding portion of the diaper better to the waist of the user, certain diapers have been provided with elastic members in the form of strips, tapes or threads fixed to at least a part of the width of the diaper and at the border of the latter between the support sheet and the top sheet. Such diapers are described in French patents FR-A-82 04 390 and 84 08 289.

However, these improvements associated with a more hermetic application of the diaper to the user do not make any contribution to provide means intended to place the inner space of the diaper in communication with the outside and in this manner to permit the passage of gaseous fluids and, thus, to ventilate the inside of the diaper to contribute to the comfort of the user.

In the prior art there are found diapers which, to arrange means of communication of their inner space with the outside when the diaper is worn, provide perforations or microperforations formed on the support sheet which normally is completely impermeable. It appears, however, that in the case of microperforations, the flow rate of gaseous fluid that the diaper can exchange with the outside is relatively low. In the case of perforations, the fluid tightness of the diaper with respect to liquid leakages is compromised, the permeability of the support sheet being too degraded.

SUMMARY OF THE INVENTION

It is an object of the invention to overcome the various aforesaid drawbacks by providing a diaper which permits good elastic application around the waist of the user while providing effective means for placing the inner volume of the diaper in communication with the outside while preventing liquid leakages.

To this end, according to the invention, there is provided a diaper characterized in that the elastic means comprise at least one strip of the elastic open foam material arranged between the support sheet and the top sheet so that the inner space of the diaper communicates with the outside of the latter through the thickness of each of the said strips.

According to other features of the invention:

Each strip extends along its width over at least a portion of the interval comprised between an edge of the pad and the neighboring edge of the diaper and each strip is fixed on one surface to the support sheet and, on the opposite surface, to the top sheet to join these together whilst leaving external and internal longitudinal edges of each of these strips to communicate respectively with the outside of the diaper and the internal space of the latter.

The outer edge of each strip and the neighboring edges of the support and top sheets are contained almost in the same plane, leaving the outer longitudinal edge of the strip visible.

The diaper comprises preferably two strips, each extending transversely over at least a portion of the length of the diaper in the neighborhood of a corresponding transverse edge of the latter.

The diaper comprises preferably two strips, each extending longitudinally over at least a portion of the length of the diaper in the vicinity of a corresponding longitudinal edge of the latter.

The foam material of each strip is water-repellent.

The foam material of each strip and the transverse section of the latter are such that the latter induces a considerable pressure drop in the flow of the liquid through the strip whilst being permeable to gaseous fluids.

The transverse section of each strip is such that, in order to have a sufficient tractive or compressive force exerted on each strip, the open cells are closed by traction or compression in order to avoid any flow of fluid.

BRIEF DESCRIPTION OF THE DRAWINGS

The invention will be better understood on reading the description which follows of an embodiment given purely by way of example and with reference to the drawings, in which:

FIG. 2 is a view in section along the ling 2-2 of FIG. 1; and,

FIG. 3 is a view in longitudinal section of a napkin in which are formed several diapers which extend longitudinally whilst being each joined through their transverse edges to the corresponding neighboring diapers.

DETAILED DESCRIPTION OF THE INVENTION

Figure 1:
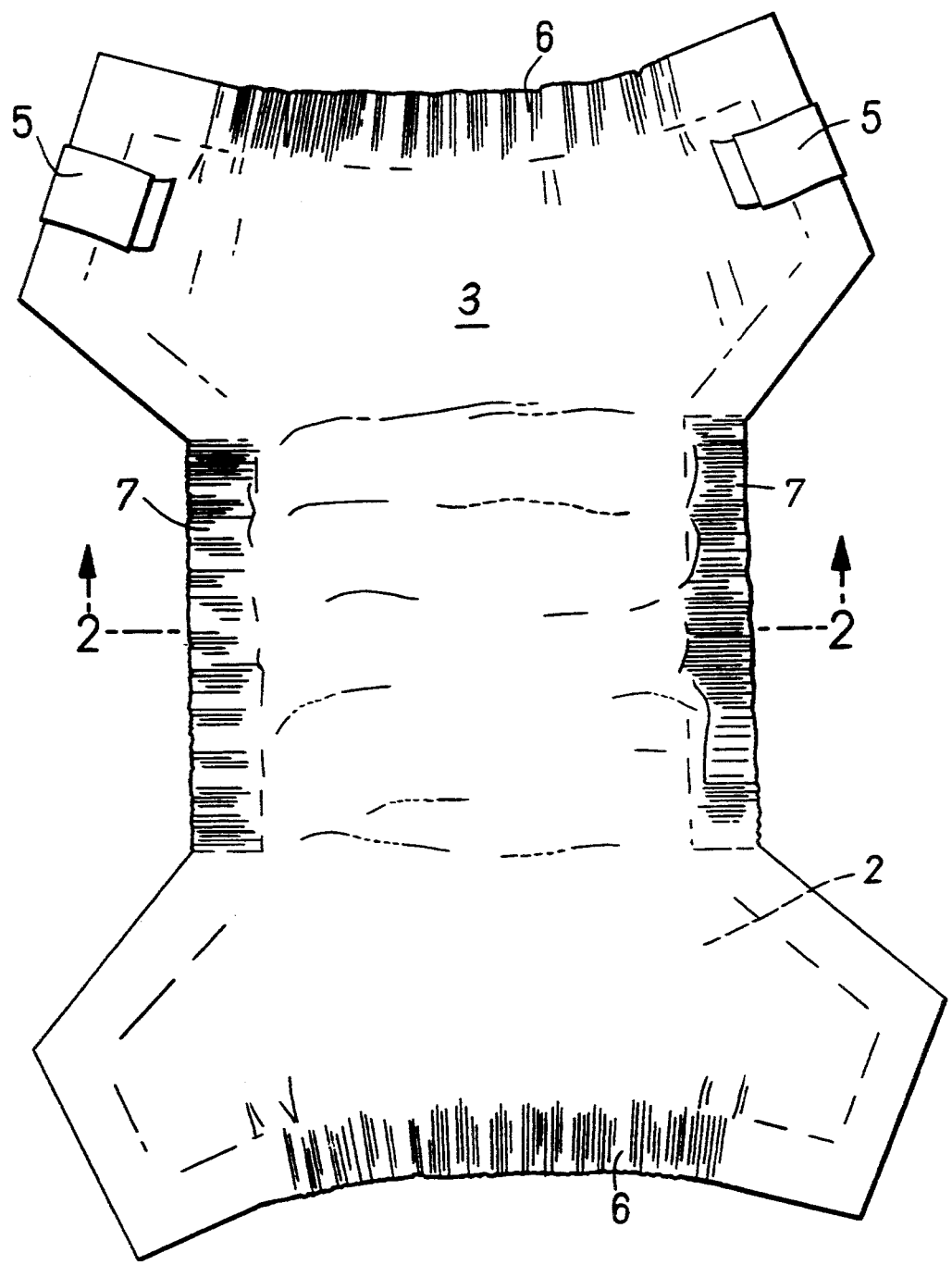
FIG. 1 is a plan view of the inner surface of the diaper according to the invention.

The diaper illustrated in the figures is intended to be thrown away after use and has a profiled shape by arranging a portion of reduced width for positioning at the level of the crotch of the user. This diaper comprises principally a flexible and impermeable support sheet 1, for example, of polyethylene, a pad 2 of absorbent material, for example, of defibered wood pulp, of cellulose wadding or any other absorbent material, such as so-called super-absorbent polymers, and a flexible and permeable top sheet, in particular permeable to urine, formed of, for example, a non-woven cloth or of perforated plastic film.

The absorbent pad 2 is placed between the support sheet 1 and tope sheet 3, the top sheet and the support being joined together over the whole of their periphery, for example, by gluing or heat-sealing, to thus enclose the pad within an internal space of the diaper bounded between the sheets.

In addition, to ensure the positioning of the diaper on the user, a fastening system is provided at one end of each longitudinal edge of the latter in the form of an adhesive tongue 5, each designed to cooperate with the support sheet 1 on a corresponding side of the opposite end of the diaper on its placing in position on the user.

The diaper comprises in addition a first elastic system formed by two elastic strips 6, each arranged along an intermediate portion of a corresponding transverse edge of the diaper and a second elastic system formed from two elastic strips 7, each extending longitudinally along a corresponding longitudinal edge of the diaper at the level of the crotch.

The strips 6, 7 of the first and second elastic systems are each fixed and tensioned between the support sheet 1 and the top sheet 3, thus forming gathered sections visible in FIG. 1.

These strips 6, 7 extend along the width over the whole of the interval comprised between the neighboring edge of the absorbent pad 2 and the corresponding edge of the diaper itself. Thus, at the level of the peripheral portions of the diaper where these strips 7 extend, the upper and support sheets are joined together through strips which are each fixed, for example, by gluing or by thermo-welding, on one of their surfaces to the support sheet 1 and, on their opposite surface, to the top sheet 3. This gluing of the strips to the sheets must be limited to the surfaces of these strips without extending into the thickness of the strips in order to avoid plugging the cells of the foam which must remain open.

The adhesion of the support sheet 1 and top sheet 3 to each strip 6 or 7 must, preferably, be such that no flow path can exist for a fluid between each of these sheets and the corresponding surface of the strips so as to avoid liquid leakages.

It will be noted, in addition, in FIGS. 2 and 3, that the outer longitudinal edge of each strip 6 or 7 and the neighboring edges of the top sheet 3 and support sheet 1 are contained within almost the same plane to leave thus visible the outer longitudinal edge of the strip, the inner longitudinal edge of the latter communicating between the sheets with the inner space of the diaper wherein the pad 2 extends. This arrangement is, in fact, obtained by cutting simultaneously the two sheets and the strips at the time of fabrication of the diaper. It is seen by referring to FIG. 3 that each strip 6 comes from a corresponding strip 6a cut out longitudinally approximately at its middle to form two strips 6, each belonging to two distinct diapers.

In FIG. 3, the diapers not yet detached from one another are assembled in one layer where they follow one another by being joined at their transverse edges, a strip 6a exrending transversely between each of these unseparated diapers by being fixed between the support sheet 1 and top sheet 3 still in the form of continuous films. From this layered structure, the diapers are then detached successively from one another by transverse cutting off along the lines C (FIG. 3) approximately at the middle of each strip 6a which has therefore a width substantially double that of each strip 6. The outer and inner longitudinal edges of the strip 6 or 7 communicate respectively with the outside of the diaper and the inner space of the latter as will be demonstrated below in the rest of the description.

In accordance with the invention, each strip 6, 7 is formed of an open cell foam elastic material, for example, of polyester, of polyester, of polyether (polyurethane) or any other suitable material.

By way of example, it is possible to use polyurethane foam of density equal to about 34 kg/m$^3$.

The role of these strips is not only to confer on the places of the diaper where they are placed, a certain elasticity intended to apply elastically and as hermetically as possible, the diaper to the corresponding parts of the body of the user, but also to permit the placing in communication of the inner space of the diaper with the outside of the latter when the diaper is worn by the user, this communication taking place through the thickness of each strip through their open cells which permits advantageous ventilation of this inner space.

The thickness of the strips 6, 7 may be comprised between about 1 and 5 mm, preferably between about 2 and 3 mm, the thickness of the strips 6 extending transversely, and preferably less than about 50 mm, the width of the strips 7 extending longitudinally being less than about 35 mm and, preferably, equal to about 25 mm.

The elasticity of the foam strips 6 must be sufficient to cover the maximum variations in waist size of the user (10 cm for an infant of about 10 to 12 kg). In addition, the thickness of the strips 6 or 7 must be sufficient to ensure good strength but must not be too great so as to limit the force necessary for elongation of each of the strips in order to preserve thus the comfort of the user and to permit the closing of the open cells by longitudinal stretching or compression of the thickness on tension of the strip or compression of the latter in order avoid forced leakages of liquid through the foam.

The porosity of the foam material and the transverse section of the strips are such that the latter induce a high pressure drop with respect to the flow of the liquid through each strip which remains permeable to gaseous fluids. This selective character of the permeability with regard to gases rather than with regard to liquids is, in addition, increased by the hydrophobic nature of the foam material which thus counters the flow of aqueous liquids upon urination.

Each strip thus ensures the fluid tightness of the application of the diaper to the body of the user and simultaneously permitting ventilation of the inner-space of this diaper.

In use, this diaper is placed on the user so that the strips 7 situated at the level of the crotch grip the thighs of this user and so that the strips 6 are applied to the waist of the latter.

The longitudinal elasticity of the foam strips permits the waist of the infant to be gripped by soft contact of the diaper around it in any position, eliminating direct leakages, a comfortable grip being also reproduced around the thighs. The elastic foam through its composition permits a notable elongation even for a width and thickness of the strip which are fairly large under the action of a weaker force with respect to other conventionally used elastic materials.

The thickness of the foam permits, moreover, a second elastic effect to the contributed by compression of the cells open in the direction of the thickness. This property improves the comfort of the user whilst eliminating the risk of leakages by pressure on the absorbent material, the cross-section of each strip being in fact such that, under the effect of a sufficient force of compression or of traction, the open cells are closed by compression or stretching of the strip respectively.

The elastic properties in extension and in compression of the strips thus permit an anti-leakage barrier to be obtained which is as effective as that which it could be hoped to obtain by means of a compact elastic material whilst showing better flexibility of application to the body of the user, which procures for the latter an important sensation of comfort.

According to yet another advantage, the use of open cell foam for the elastic strips enables the ventilation of the inner space of the diaper while resisting passages of fluids.

Although the example of the diaper previously described to illustrate the invention comprises an elastic system intended to grip the waist of the user and elastic system intended to grip the thighs of the latter, it is clear that one or other of these elastic system may be used independently of the other.

However, the preferred embodiment of the invention recommends placing the open cell foam strips previously described at the level of the transverse edges of the diaper to the extent that it is this spot, intended to be applied to the waist of the user, that the foam strips will place most effectively their role of means of communication of the inner space of the diaper with the outside. In fact, the open cells of the foam strips provided on the longitudinal edges of the diaper have, when the latter is worn by a user, a tendency to be held closed when the crotch of the diaper is applied hermetically around the thighs and the corresponding strips are then stretched. The thighs are only subjected to a slight variation in circumference as a function of the different positions of the user, the state of initial tension of the foam strips provided the level of the crotch is hence always more or less substantially preserved and, for this reason, the cells have less tendency to be kept open.

On the other hand, when these foam strips are placed on the transverse edges of the diaper, they become applied to the waist of the user and it is well known that, at the level of the abdomen, the body varies notably in circumferences as a function of the respiratory movements or abdominal muscular contractions. These variations in circumference permit, even if the diaper has been applied in a stretched manner around the waist, the corresponding foam strips to be substantially relaxed and thus permit at least periodically the opening of the cells if the later are otherwise closed and favor the ventilation of the inner space of the diaper.

The diaper may be of any conventionally known general shape, other than those previously described, for example, rectangular, in the form of an H or with any other anatomical cutout. According to another modification, a space may be formed between one elastic strip and the neighboring edge of the absorbent pad if the inner longitudinal edge of the strip can communicate with the inner space of the diaper. According to another modification, the outer edge of one elastic foam strip may be stretched more at the inside or more at the outside of the neighboring edges of the top and support sheets with respect to the diaper, the essential thing being that the outer longitudinal edge of this strip should communicate with the outside of the diaper.

It is well understood that the invention is not limited to use for babies, but can also be used by a user of any age, for example, an incontinent adult, the dimensions of the diaper being then adapted to the corpulence of the user.

We claim:

1. A diaper comprising a flexible and impermeable support sheet, a flexible and permeable top sheet, an adsorbent pad arranged between said top sheet and said support sheet of lesser dimension than said top sheet and said support sheet, a pair of elastic strips between said top sheet and support sheet and outwardly of said absorbent pad, said elastic strips comprising waist seals, said support sheet being made of polyethylene, said top sheet being made of a non-woven material, said absorbent pad being made from a material selected from the group consisting of defibered wood pulp, cellulose wadding and superabsorbent polymer, said elastic strips being formed from an open cell material, said support sheet and said top sheet being joined together over the whole of their periphery by an adhesive to enclose said pad within an internal space, and the cells of said open cell material remaining open without being plugged by said adhesive.

2. A diaper comprising a flexible and impermeable support sheet, a flexible and permeable top sheet superimposed over said support sheet, said support sheet and said top sheet being peripherally joined together to create an inner space therebetween, said support sheet and said top sheet being generally H-shaped with extended end sections joined to an intermediate indented crotch section, each of said end sections having a transverse edge, each of said end sections having a first pair of corners along said transverse edge of said sheets and a second pair of corners longitudinally inwardly of said first pair of corners, an absorbent pad in said inner space, said absorbent pad being thicker than each of said top sheet and said support sheet, a first pair of elastic strips mounted between and connected to said support sheet and said top sheet at opposite edges of said crotch section, leg seals formed at the location of said first pair of elastic strips when said diaper is mounted about a user, said first pair of elastic strips being exposed to said inner space, a second pair of elastic strips mounted between and connected to said support sheet and said top sheet at opposite transverse edges of said end sections, waist seals formed at the location of said second pair of elastic strips when said diaper is mounted about a user, said second pair of elastic strips being exposed to said inner space, said elastic strips being in a gathered condition, said leg seals and said waist seals at said elastic strips being breathable and gas permeable to provide ventilation and being resistant to the permeability of fluid to minimize any urine from leaking from said diaper when said diaper is mounted about a user, and fasteners at opposite ends of one of said end sections for detachable securement to the other said end sections while overlapping said other of said end sections to detachably mount said diaper about a user.

3. The diaper as claimed in claim 2, wherein said first pair of elastic strips being coplanar with said pad and second pair of elastic strips being coplanar with said pad.

4. The diaper as claimed in claim 2, wherein said first pair of elastic strips being exposed to said inner space without any structural members between and said second pair of elastic strips being exposed to said inner space without any structural members therebetween.

5. The diaper as claimed in claim 3, wherein said first pair of elastic strips being exposed to said inner space without any structural members therebetween and said second pair of elastic strips being exposed to said inner space without any structural members therebetween.

* * * * *

UNITED STATES PATENT AND TRADEMARK OFFICE
CERTIFICATE OF CORRECTION

PATENT NO. : 5,435,806
DATED : July 25, 1995
INVENTOR(S) : Daugan et al.

It is certified that error appears in the above-indentified patent and that said Letters Patent is hereby corrected as shown below:

column 4, line 26, "exrending" should read --extending--.

column 5, line 13, "tighness" should read --tightness--.

Signed and Sealed this

Nineteenth Day of December, 1995

Attest:

BRUCE LEHMAN

Attesting Officer     Commissioner of Patents and Trademarks